(12) United States Patent
Peters et al.

(10) Patent No.: US 6,214,561 B1
(45) Date of Patent: *Apr. 10, 2001

(54) METHOD FOR DETECTING BIOLOGICALLY ACTIVE COMPOUNDS FROM COMPOUND LIBRARIES

(76) Inventors: Thomas Peters, Luebecker Str. 16, D-23909 Ratzeburg (DE); Bernd Meyer, Glashutter Weg 84, D-22844 Norderstedt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,344

(22) Filed: Nov. 25, 1997

(30) Foreign Application Priority Data

Nov. 28, 1996 (DE) .............................................. 196 49 359

(51) Int. Cl.$^7$ ........................ G01N 33/53; G01N 33/566; G01N 33/543; G01N 24/00

(52) U.S. Cl. ........................... 435/7.1; 436/501; 436/517; 436/518; 436/519; 436/173

(58) Field of Search .............................. 435/7.1; 436/501, 436/517, 518, 519, 173

(56) References Cited

U.S. PATENT DOCUMENTS

| 5,459,077 | * | 10/1995 | Moore et al. | 436/173 |
| 5,698,401 | * | 12/1997 | Fesik et al. | 435/7.1 |

FOREIGN PATENT DOCUMENTS

| WO95/25737 | 9/1995 | (WO) | C07H/21/00 |
| WO 96/22530 | 7/1996 | (WO) | G01N/33/53 |

OTHER PUBLICATIONS

Balaram, et al., "Negative Nuclear Overhauser Effects as Probes of Macromolecular Structure", *Journal of the American Chemical Society* vol. 94:11, pp. 4015–4017 (May 1972).

Overhauser, A.W., "Paramagnetic Relaxation in Metals", *Physical Review* vol. 89 No. 4, (Feb. 1953).

Youngquist, R.S. et al., "Matrix–assisted Laser Desorption Ionization for Rapid Determination of the Sequences of Biologically Active Peptides Isolated From Support–bound Combinatorial Peptide Libraries", *Rapid Communications in Mass Spectrometry*, vol. 8 pp. 77–81 (1994).

* cited by examiner

Primary Examiner—Bennett Celsa
Assistant Examiner—Maurie E. Garcia
(74) Attorney, Agent, or Firm—Oppenheimer Wolff & Donnelly, LLP; Claude A. S. Hamrick

(57) ABSTRACT

A method for detecting at least one substance (a ligand) present in a compound library using at least one additional substance (a receptor) that binds to the ligand comprises adding to the compound library such a receptor that has substantially higher molecular weight than the ligand to be identified, and performing of such a spectroscopic measurement technique with the mixture, without isolating the receptor-ligand complex, that can detect those dipolar resonance phenomena which occur upon a binding of a receptor to a ligand.

19 Claims, 4 Drawing Sheets

Disaccharid 1

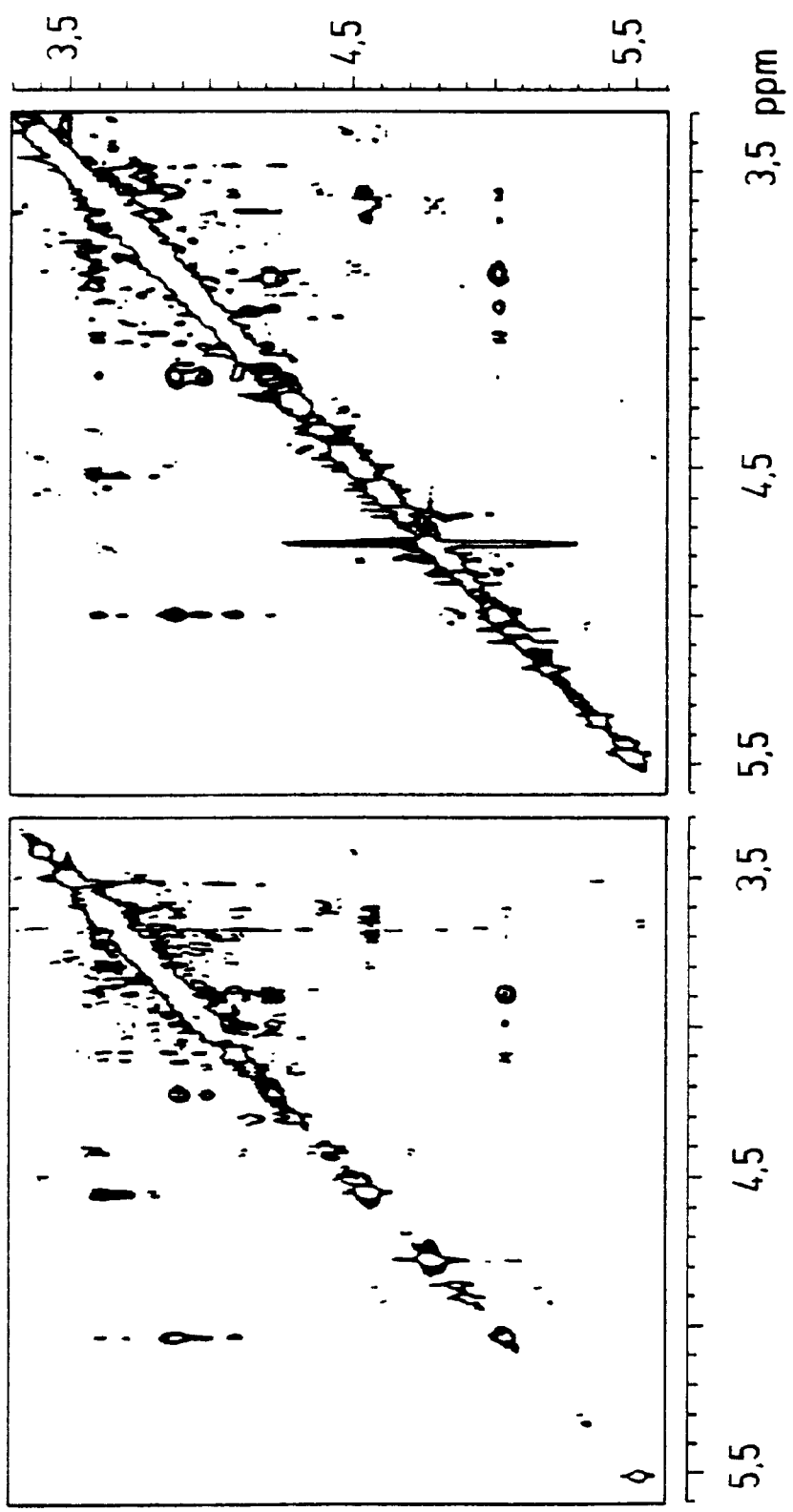

METHOD FOR DETECTING BIOLOGICALLY ACTIVE COMPOUNDS FROM COMPOUND LIBRARIES

FIELD OF THE INVENTION

This invention relates to a method for detecting at least one compound (a ligand) in a compound library using at least one other compound (a receptor) that binds to the ligand.

BACKGROUND OF THE INVENTION

Such methods are common in the biochemical laboratory praxis.

A compound in the sense of the present invention can be a molecule, an aggregate or a complex composed of many like or dislike molecules and/or atoms.

A ligand that binds to a receptor, and therefore shows binding affinity for this receptor, is called a biologically active compound.

Compound libraries which are also called combinatorial libraries are synthetic or natural mixtures that contain a number of different compounds. In most cases, identity and quantity of particular compounds in the library are not known, the procedure, however, that led to these mixtures is often known. Such compound libraries can either consist of one sort of compounds, e.g. peptides or organic synthetic compounds, or they can comprise several different components, e.g. plant extracts. Also, complex components such as whole viruses, bacteria or cells can be part of a compound library.

Especially in drug research compound libraries play an important role when compounds are to be identified from complex mixtures for drug targets or when new biologically active substances have to be identified in such complex mixtures.

Such investigations are called "screening of compound libraries". The screening, i.e. the investigation whether an interesting compound or compound with potentially interesting properties is part of a compound library, is performed using a receptor. A receptor is the fishing pole, that allows to fish the ligand out of the compound library.

Many different methods to screen compound libraries have been developed in pharmaceutical research and development as well as in biochemical and medical basic research. Common methods are e.g. the ELISA-test, the RIA-test, the affinity chromatography or different well known blotting methods such as Western-, Northern- or Southern-Blot.

All these methods have in common that with the help of the receptor the ligand in the compound library is spatially separated from the other compounds in the library. The spatial separation can take place during or after binding of the receptor to the ligand. The spatial separation is achieved by immobilizing one of the partner (either the receptor or the components of the compound library) to a solid support. Such supports are mostly microtiterplates, chromatography resins, beads, or filter papers.

In many cases it is also necessary to label one of the molecules in the study by using radioactive or non-radioactive isotopes in order to detect the receptor-ligand complex. Alternatively, a specific detection tool, e.g. an antibody, can be used to detect the receptor-ligand complex.

Affinity chromatography is widely used for screening of compound libraries by utilizing a receptor that is immobilized on a chromatography resin, which in turn is used to produce a chromatography column. If a compound library, which contains a ligand for the immobilized receptor, is passed over this column the ligand specifically binds to the immobilized receptor and by this process can be separated from the other compounds in the library. Subsequent detection of the ligand is achieved by elution of the ligand from the column and specific detection reactions.

Detection reactions can be based on detection of a ligand with a specific antibody, or if the ligand was labeled, on detection of the label.

In many cases it is not possible to label the compounds of a library, and also in many cases no specific antibodies exist. This is especially true if a new ligand in a compound library has to be identified.

In such cases a chemical analysis has to be performed, e.g. sequencing reactions that at present time are only applicable to nucleic acids and peptides.

A ligand that has been separated from the compound library with the help of a receptor can also be analyzed by mass spectrometry. In the recent past this method was increasingly used to analyze compound libraries.

An example for such a method is described in the publication "Matrix-assisted laser desorption ionization for a rapid determination of the sequences of biologically active peptides isolated from support-bound combinatorial peptide libraries" of Youngquist et al., 1994, Rapid Communications in Mass Spectrometry, No. 8, Pages 77–81.

Here a special mass spectrometry technique, the "matrix-assisted laser desorption ionization" (MALDI) was used to isolate such peptides from the synthetic peptide library, that are potentially useful to inhibit infections with the HI-virus.

In that procedure the peptide library was automatically synthesized on a solid support in form of inert plastic beads carrying of random peptide sequences. The peptides were immobilized on beads. Biological activity was tested by using a monoclonal antibody, that was directed against a surface protein of the HI-virus. Beads that were bound to the antibody were detected by an enzyme-conjugated staining method known from ELISA and by immunoblotting techniques. Colored beads were isolated and peptides were cleaved off. These peptides were analyzed with MALDI, which allows a direct sequencing and, therefore, identification of the peptides.

Each step of this method shows fundamental disadvantages that are also characteristic for the other methods known for detecting of specific ligands in compound libraries. All these methods are based on the principle that the receptor in a complex with the ligand is spatially separated from the other components of the compound library. The spatial separation requires either immobilization of the ligand as described in the publication mentioned above or immobilization of the receptor, e.g. in the affinity chromatography where the receptor is bound to a solid support.

This immobilization represents a considerable problem because biologically active receptors are often inactivated by immobilization.

The receptor binding sites for ligands are usually located on the surface. Therefore, these binding sites can participate in the immobilization reaction and it is impossible to control which sites of the receptor are used for the immobilization. In fact, in many cases the receptor binding site is directly coupled to the support and, thus, the binding site is no longer accessible for the ligand.

Another problem occuring in the immobilization of particularly protein receptors is denaturation, i.e. a conformational change of a receptor, that leads to loss of binding affinity.

It cannot be predicted whether all compounds in an immobilized library are equally well immobilized and which of the compounds are still active after immobilization. This is risky, because biologically active compounds present in the library may not be immobilized and therefore would not be detected with this process. In such a case the detection reaction is negative even though a bioactive ligand was present in the compound library.

Known processes have another major disadvantage in that they are complicated and lengthy. After immobilization of the ligand or the receptor many washing steps are necessary to remove non-immobilized molecules and only thereafter can the compound library be incubated with the receptor. Washing steps are again necessary after incubation to remove unbound material. Subsequently, complicated analytical procedures such as immunostaining or, after separation of the analyte from the solid support, mass spectrometric analysis has to be performed.

Immunostaining methods usually require specific antibodies against the ligand. This is impossible if new ligands are to be found and difficult if ligands are to be investigated that are not proteins.

An alternative to immunostaining is the radioactive or non-radioactive labelling of compounds in the library. Only nucleic acid libraries can be labelled without problems. For all other classes of compounds either no labelling technique is known or the labelling technique has major disadvantages. For instance, radioactive labelling of proteins via iodination is a considerable health risk.

A further complication arises from the fact that compound libraries may contain a couple of compounds that display equal or similar binding affinity for the receptor. These compounds are then isolated as a mixture and cannot easily be analyzed with the known methods.

A further disadvantage of known methods is that it is impossible to analyze the conformation, i.e. 3D-structure of the bound ligand or the receptor ligand complex.

In the context described above, it is therefore object of the present invention to provide a method for detecting compounds in a compound library, that is much simpler and faster than the known methods, and that would neither require immobilization or labelling of receptor and/or ligand, nor the spatial separation of the receptor ligand complex from all other compounds in the compound library.

BRIEF DESCRIPTION OF THE PRESENT INVENTION

According to the invention this object is achieved by performing a method with the following steps:
a) adding a receptor to the compound library that has a substantially higher molecular weight than the ligand to be detected, and
b) performing of such a spectroscopic measurement technique with the mixture resulting from step a), without isolating of the receptor-ligand complex, that can detect those dipolar resonance phenomena which occur upon a binding of a receptor to a ligand.

The inventors have realized that it is possible to directly detect a ligand in a compound library with known spectroscopic techniques that measure those dipolar resonance phenomena which occure if and only if a receptor with a much higher molecular weight than the ligand to be detected binds to a ligand.

Dipolar resonance phenomena are based on the resonance interaction between dipoles and electromagnetic waves with which a sample is radiated. Dipolar interactions depend on the mobility of the molecule that contains the dipoles. The molecular mobility in turn is dependent on whether the molecule is free in solution or whether it is associated with a larger molecule that is e.g. a complex. If a smaller ligand binds to a large receptor the molecular mobility is governed by the large receptor. Only biologically active compounds can bind to the receptor. The fact that the binding has occured becomes detectable because the receptor, with a much higher molecular weight, is responsible for the properties of the ligand-receptor complex.

Surprisingly, it turned out that this phenomenon can also be used to detect the binding of a receptor to a ligand even if a number of other substances is present in the solution that is investigated. If the receptor specifically binds to a ligand signals are measured upon addition of a receptor to a compound library that can be discriminated from all other measured signals. If no binding occurs, these specific signals are not measured and it must be deduced that the compound library contains no ligand for the receptor.

With that method it is not necessary to immobilize either receptor or ligand. It is also not necessary to modify or label either receptor or ligand. This does not only save complex experimental steps but it also removes the risk of biological inactivation, which may occur during such steps.

The spectroscopic detection of the receptor-ligand interaction in the compound library takes place directly after addition of the free receptor in solution and therefore, the natural (native) conformation of all molecules involved is observed. This garantuees that the binding sites exposed in vivo are accessible and conserved. It follows, that the receptor ligand interaction takes place without the influence of experimental conditions.

The binding reaction can even be detected if additional molecules are necessary for this binding, and if these molecules are also present in the compound library. For example, this is important for allosteric enzyme reactions in which binding of an enzyme to a substrate is influenced by other molecules, so-called allosteric effectors.

A considerable advantage of the invented method is that the isolation of a receptor-ligand complex, i.e. the spatial separation of this complex from all other substences in the library is no longer necessary. This time consuming step has to be optimized for each individual experiment. Using the method of the invention it has become much faster and simpler because there is no need for isolation of the receptor ligand complex. Moreover, losses inherent in such separation techniques are avoided.

Using the method of the invention the question if an interesting ligand is present in a compound library can be answered with a minimum of experimental effort and standard spectroscopic equipment. Thus, the method is very well suited to perform screening of compound libraries.

Compound libraries can be tested for a compound that in principle is known but that is spectroscopically not identifiable in presence of the other components of the library. It is now possible to identify the compound (ligand) in question, because after binding to the receptor the spectroscopically accessible properties are now characteristically influenced by the receptor.

The spectroscopic properties of the ligand are now different from those of the compound library as such and they are also different from the spectroscopic properties of the unbound receptor. Therefore, in this case compound libraries can be tested for a compound in question routinely and after addition of the receptor.

It is also possible to test a compound library whether an active compound is present at all, because only this compound will bind to the receptor. The dipolar resonance phenomena that are caused by this binding occur in the spectra and can in principle be assigned to a certain compound (ligand) if suitable measurement techniques that are capable to record this dipolar resonance phenomena are applied.

In a preferred embodiment of the invention an NMR (Nuclear Magnetic Resonance) spectroscopy is used as spectroscopic measurement technique.

Here, it is advantageous, that this method has already been known for many years and has developed into a routine method. Accordingly, many places operate standard NMR spectrometers that can be used to perform the invented method. Most frequently, NMR is used to determine the resonance signals of protons that are usually present in biologically active molecules in large numbers. Protons have a large magnetic moment. After binding to the receptor resonance phenomena occur that are characteristic. Therefore, practically all biologically interesting molecules are accessible to the invented process via a well established technique.

In a particular preferred embodiment of the invention the transfer Nuclear Overhauser Effect (trNOE) is utilized to measure the dipolar resonance phenomena.

This embodiment is based on the Nuclear Overhauser Effect (NOE; the NOE was first described as a generalized effect in "Paramagnetic Relaxation in Metals", 1953, Physical Review 89, Pages 689–700). As a consequence of the NOE NMR signals are enhanced. The Nuclear Overhauser Effect is based on dipolar interactions between nuclear spins, e.g. protons, through space.

The enhancement that is caused by the NOE depends on the distance of the nuclei that are connected by dipole-dipole-interaction and it depends on time. Dipolar couplings between protons are dependent on molecular mobility and dipolar couplings are totally different for low molecular weight compounds compared to high molecular weight compounds. If a ligand binds to a receptor that has a much higher molecular weight than the ligand so-called transfer NOE are observed for that ligand, because its molecular mobility is now determined by the higher molecular weight receptor (trNOE, described in "Negative Nuclear Overhauser Effects as Probes of Macromolecular Structure", 1972, Journal of the American Chemical Society, 94, Pages 4015–4017). In other words, the receptor transfers specific spectroscopically detectable properties to the ligand that on the one hand reflect the fact that binding has occured, and on the other hand which compound (ligand) has binding affinity to the receptor.

The measurement of trNOEs has the advantage, that it allows to discriminate compounds that bind to a receptor from those that do not bind to a receptor with high sensitivity and selectivity. This is true even if both are members of the same compound library and even if the compound library is a complex mixture of very different components.

In a preferred embodiment of the invention the transfer Electron Nuclear Overhauser Effect is measured as a dipolar resonance phenomenon. Here, the exchange of dipolar polarization between electrons and nuclei with magnetic moments is measured. This effect occurs for instance, if ligands or receptors are radicals and a binding reaction occurs.

Here, it is of advantage that significant changes in signal intensities can be observed that in turn allow conclusions about the nature of the bound state.

In the following the transfer Nuclear Overhauser Effect and the transfer electron Nuclear Overhauser Effect will be summarized under the acronym trNOE.

In a further embodiment of the invention the trNOE is measured utilizing two-dimensional NOE-spectroscopic experiments (2D-NOESY or 2D-ROESY).

In 2D-NOESY or 2D-ROESY experiments a two-dimensional NMR-spectrum is recorded, i.e. a spectrum that has two frequency axes. The intensities of the observed signals, the so-called "crosspeaks", represent a third dimension.

A two-dimensional experiment consists of several periods, the first being the so-called preparation period, the second the so-called evolution or mixing period, and finally the detection period in which an interferogram (FID) is recorded. The time variable of the evolution period is called $t_1$, which designates a variable waiting time that ranges from microseconds to seconds and during which chemical shifts and spin-spin couplings evolve. The mixing period follows the evolution period or in some cases interrupts it. During the mixing period dipolar resonance phenomena evolve. The mixing time is constant, whereas the evolution time $t_1$ is changed during the experiment. After evolution and mixing period the detection period takes place with a time variable $t_2$, that again is constant. The data that are recorded with a two-dimensional NMR experiment are often represented in a so-called contour diagram. A contour diagram shows cuts through the signal mountains at a given height, i.e. through the crosspeaks of the spectrum.

The measurement of trNOEs in 2D-NOESY-experiments has the advantage that a large spectral resolution is achieved which in turn allows separation or spreading of the signals. Therefore, especially for complex compound libraries trNOEs can be detected specifically and at low concentration of the ligand in question.

These two-dimensional experiments can also be performed as part of multi-dimensional experiments.

It is obvious that any number of evolution times can be kept constant and that the dimensionality can be reduced in this way.

In a further embodiment of the invention the trNOE is measured as part of a multi-dimensional homo- or heteronuclear experiment.

Such an experiment can be e.g. a 3D-HMQC-NOESY, a 3D-NOESY-NOESY, or a 4D-TOCSY-NOESY-HSQC (HMQC =Heteronuclear Multiple Quantum Coherence, TOCSY=Totally Correlated Spectroscopy, HSQC= Heteronuclear Single Quantum Coherence).

For such multi-dimensional experiments it is of advantage that the spectral resolution is further enhanced.

It is obvious that all NMR experiments mentioned above can also be performed in a rotating coordinate system. Then the trNOE is designated as trROE.

Furthermore, techniques can be used to lower the dimensionality of the experiment or to yield special effects where one or several evolution times are kept constant or one or several radio frequency pulses are used in a selective or band selective fashion.

Here, it is advantageous to improve the resolution, e.g. by acquiring more datapoints, so that the measurement time and therefore the duration for each single experiment is shortened and noise is minimized. If the trNOE is measured in a one-dimensional experiment the advantage is that the analysis of the spectra is especially simple.

In another embodiment of the invention the 2D-NOESY-spectrum of the compound library in the presence of the receptor is acquired with a short mixing time that is smaller than approximately 500 ms.

This has the advantage that an especially good signal to background ratio is obtained, in other words the noise is minimized. As a consequence of this the crosspeaks characteristic for the bound ligand will appear even clearer to furthermore facilitate their detection.

In another embodiment of the invention fluorescence spectroscopy is used as the spectroscopic measurement technique.

This is useful if the compounds to be detected exhibit flourescence, e.g. if absorbed energy is emitted again in form of radiation after extremely short periods of time following excitation through light or other electromagnetic radiation.

Flourescence spectroscopy has the advantage that it is an extremely sensitive technique, especially if laser induced flourescence is detected. In this case also the bound receptor influences the flourescence spectrum characteristically.

In a further embodiment of the invention ESR (Electron Spin Resonance) spectroscopy is used.

ESR-Spectroscopy is also called EPR-Spectroscopy (Electron Paramagnetic Resonance). This technique is based on the fact that for electrons upon irradiation with an electromagnetic wave of a certain frequency magnetic resonance absorption occurs and the magnitude of this absorption is measured. This technique has the advantage that it is one of the most common spectroscopic methods.

In a preferred embodiment of the invention the ligand is a low molecular weight compound with a molecular weight of less than approximately 2000 Da, and the receptor is a high molecular compound with a molecular weight that is larger than approximately 5000 Da.

Using this methodology it is especially advantageous that significant trNOEs are detected because, given the large ratio of the molecular weight of the receptor to the molecular weight of the ligand, the NOE of the ligand is completely determined by the NOE of the receptor. In such cases especially characteristic spectra are measured that make the detection of binding extremely easy.

In this respect it is of further advantage that pharmaceutically important compounds, particularly so-called lead substances, have low molecular weights (MW<1000 to 2000), e.g. hormones, antibiotics, enzyme inhibitors, etc. The receptors, in most cases proteins, have high molecular weights that in most cases are much higher than 15000 Da.

The receptor can consist of many high molecular weight compounds or can be embedded into a higher molecular aggregate or can be included in whole cells or in cell fragments.

Furthermore, it is possible to perform control experiments for each spectroscopic technique. For this purpose e.g. inhibitors for the receptor ligand binding can be used. After addition of the inhibitor the corresponding trNOE must no longer be detectable.

Following this protocol, it is also possible to test the specificities of the receptor-ligand binding. This is especially important if the compound library contains several ligands with binding affinities for the receptor.

The compound library comprises natural substances that are chosen from peptides, proteins, nucleic acids, carbohydrates, lipids, whole cells, organelles, cell exstracts, whole bacteria, bacterial extracts, whole viruses, virus extracts or body fluids or mixtures thereof.

Here it is of advantage that the method of the invention allows to test complex compound libraries such as natural product mixtures or cell extracts directly without preliminary separation of the components or isolation of individual components. Therefore, the method is getting simpler and faster in practice.

In a further embodiment compound libraries with chemically synthesized compounds are used. The compounds can comprise peptides, oligonucleotides or other molecules that have been derived from organic synthesis and, again, no homogenous mixture is required.

In pharmaceutical research drugs that are already known are often chemically modified and a control is required of whether the modified form is still biologically active. Using the method of the invention it is now possible to test complete mixtures of several different modified forms in one experiment for their biological activity. This requires neither a preliminary separation e.g. of synthetic products of different size nor is it required that the drugs are chemically homogenous. In this respect it is important to mention peptide libraries that are used to inhibit naturally occuring receptors in the body or to inhibit viruses or other pathogens. In each of these cases the interaction between a low molecular weight ligand and a high molecular weight receptor plays a crucial role that can be quickly tested with the invented process.

It is obvious that also mixtures of natural and synthetic compounds can be used as compound libraries for the invented process.

Unknown ligands are identified with the help of additional one- or multi-dimensional NMR experiments.

This opens the possibility to screen compound libraries for new ligands of well known receptors. In general, such a protocol makes use of 2D-NOESY or 2D-ROESY experiments and, subsequently, on the basis of the data obtained (spectra, crosspeaks) further two- or multi-dimensional NMR experiments such as the so-called COSY, TOCSY or HMQC experiments are performed. These NMR techniques, which are known to the experts, can also be performed in the form of 3D-NMR experiments or preferably as 1D or 2D variants of 3D experiments.

Furthermore, the same protocol allows not only to identify new ligands but also to analyze the structures of already known ligands or of new ligands in the receptor-bound state.

Such an approach toward structural analysis has the advantage that the biologically active conformation of a ligand, i.e. the conformation in the receptor-bound state can be analyzed without prior crystallization or other chemical treatment of the ligand. Furthermore, this method is much more sensitive and requires less amounts of substances than the standard methods for structure elucidation.

In a further embodiment of the invention neural nets are imployed.

Neural nets are programs that are modeled after the structure and function of the nerve system of living organisms. Such programs show much higher power than common programs, especially for complex problems such as pattern recognition and learning.

In this context it is of special advantage that neural networks have properties that allow the extraction of information from spectra even in the presence of extremely strong background signals. This background can be higher than the signals by a factor of 10. Also, spectrum recognition with the neural networks comprises the ability to recognize individual components in spectra of mixtures. This property is of special importance if several molecules at the same time undergo approximately equally strong ligand-receptor binding reactions.

In this respect it is of further advantage that the sensivity of the method can be enhanced both during the measurement as well as during the evaluation of the results of the measurement. Especially, for the evaluation of complex two-dimensional spectra it is of advantage to have powerful computer programs available that allow to extract the important crosspeaks from the experiment.

It is obvious that the characteristics explained above and below are not only valid in the combinations explicitly mentioned, but also in any other combination or alone without leaving the scope of the present invention.

BRIEF DESCRIPTION OF THE DRAWINGS

In the following, the invention will be explained by way of an example selected from the practice in connection with the drawings, in which

FIG. 3a shows a 2D-trNOESY-spectrum of a mixture of FIG. 2a after addition of the receptor AAA;

FIG. 3b shows a 2D-trNOESY-spectrum of a mixture of FIG. 2b after addition of the receptor AAA.

DETAILED DESCRIPTION OF THE INVENTION

Screening of two disaccharide compound libraries with the help of a lectin (receptor) utilizing the trNOE-effect A particular disaccharide 1 (ligand) that is present in two compound libraries of different complexity is identified with the help of a protein receptor, in this case a lectin, utilizing the method of the invention. Disaccharide 1, α-L-Fuc-(1→6)-β-D-GlcNAc-OMe, consists of a fucose residue and a substituted glucosamine residue.

Figure 1:
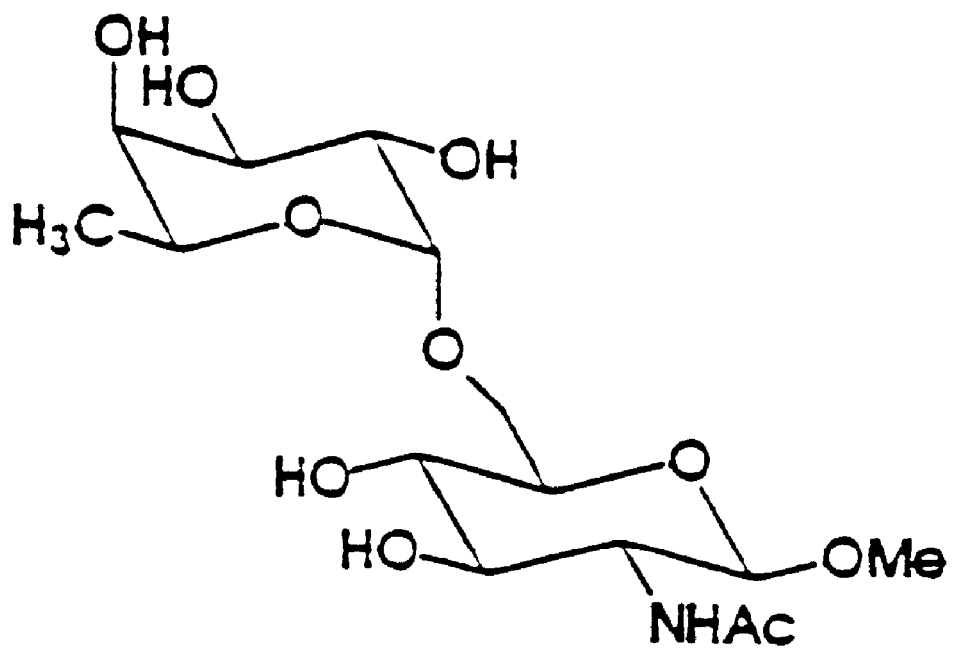
FIG. 1 shows the chemical formula of a low molecular weight disaccharide (ligand), i.e. α-L-Fuc-(1→6)-β-D-GlcNAc-OMe, that is bound by the lectin Aleuria Aurantia Agglutinin (receptor AAA)

Disaccharide 1 that is shown in FIG. 1 is present in two different compound libraries A and B that consist of 6 and 15 different carbohydrate derivatives, respectively. A composition of the saccharide libraries is shown in Table 1.

TABLE 1

Composition of the Compound Libraries

| Oligosaccharide | Library A (concentration in M) | Library B (concentration in M) |
|---|---|---|
| α-D-Man-OMe | $1.9 \times 10^{-2}$ | $1.9 \times 10^{-2}$ |
| α-D-Glc-OMe | $1.9 \times 10^{-2}$ | $1.9 \times 10^{-2}$ |
| β-D-Gal-OMe | $1.7 \times 10^{-2}$ | $1.7 \times 10^{-2}$ |
| β-D-Gal-(1→4)-β-D-Glc-Ome | $0.7 \times 10^{-2}$ | $1.6 \times 10^{-2}$ |
| Saccharose | $1.0 \times 10^{-2}$ | $1.0 \times 10^{-2}$ |
| α-L-Fuc-(1→6)-β-D-GlcNAc-Ome (Disaccharide 1) | $1.0 \times 10^{-2}$ | $1.0 \times 10^{-2}$ |
| D-Mannitol | — | $1.6 \times 10^{-2}$ |
| D-Raffinose | — | $0.9 \times 10^{-2}$ |
| D-Lactitol | — | $0.9 \times 10^{-2}$ |
| D-Maltitol | — | $0.9 \times 10^{-2}$ |
| α-D-Gal-Ome | — | $1.5 \times 10^{-2}$ |
| β-D-Gal-(1→4)-β-D-Glc-Oall | — | $0.8 \times 10^{-2}$ |
| β-D-Gal-(1→4)-β-D-Glc-Obzl | — | $0.8 \times 10^{-2}$ |
| α-D-Man-(1→2)-α-D-Man-Ome | — | $1.0 \times 10^{-2}$ |
| β-D-Gal-(1→2)-β-D-Gal-Ome | — | $1.0 \times 10^{-2}$ |

It is known, that the lectin Auleuria Aurantia Agglutinin (AAA) binds to disaccharide 1. For the other components of the compound library it was not known whether they exhibit binding affinity for the lectin or not.

The following experimental conditions were chosen:

NMR-spectra of compound libraries A and B were recorded on a BRUKER DRX 500 spectrometer with a spectrometer frequency of 500.13 MHz and a temperature of 310 K. For the preparation of the samples the two libraries A and B were disolved in 80 μl $D_2O$ each. 40 μl of each solution of the libraries A and B were then diluted into 500 μl $D_2O$. These samples were used for NMR experiments where no receptor (lectin, AAA) was present.

The residual 40 μl were mixed with 500 μl of 0.5 mM solution of the lectin (receptor AAA) in $D_2O$ each. These samples were used for the measurement of trNOEs.

The concentration of oligosaccharide ligands in all samples was approximately 10 mM for each component and this led to a molar ligand to receptor ratio of approximately 20:1.

Phase sensitive 2D-NOESY-spectra were acquired with the standard pulse sequence, that is:

$$\pi/2 - t_1 - \pi/2 - \text{mixing time} - \pi/2 - t_2.$$

$t_1$ corresponds to the evolution period, $t_2$ to the detection period as this has been explained before. The HDO-signal (i.e the background residual signal of water) was presaturated with low power irradiation. The 2D-NOESY-spectra for the libraries A and B in the absence of lectin were acquired with 512 data points in $t_1$ and 2K (library A) or 4K (library B) data points in $t_2$. 32 scans were acquired each. After zero-filling and Fourier-transformation 4K×2K data matrices were obtained. Relaxation delays were 4.4 s (library A) or 3.6 s (library B). Mixing times were 900 ms in both cases. The spectral widths were 2.740 Hz (library A) and 4.496 Hz (library B).

For the trNOESY-spectra of both libraries in the presence of lectin 640 experiments in $t_1$ and 4K datapoints with 32 scans each in $t_2$ were acquired. Zero-filling and Fourier-transformation yielded 4K×2K spectra. After the first π/2pulse a spinlock field of approximately 3.5 KHz was switched on to supress disturbing signal background from protein signals. The mixing time was 400 ms and the spectral width was 2.379 Hz for both spectra.

Figures 2A, 2B:
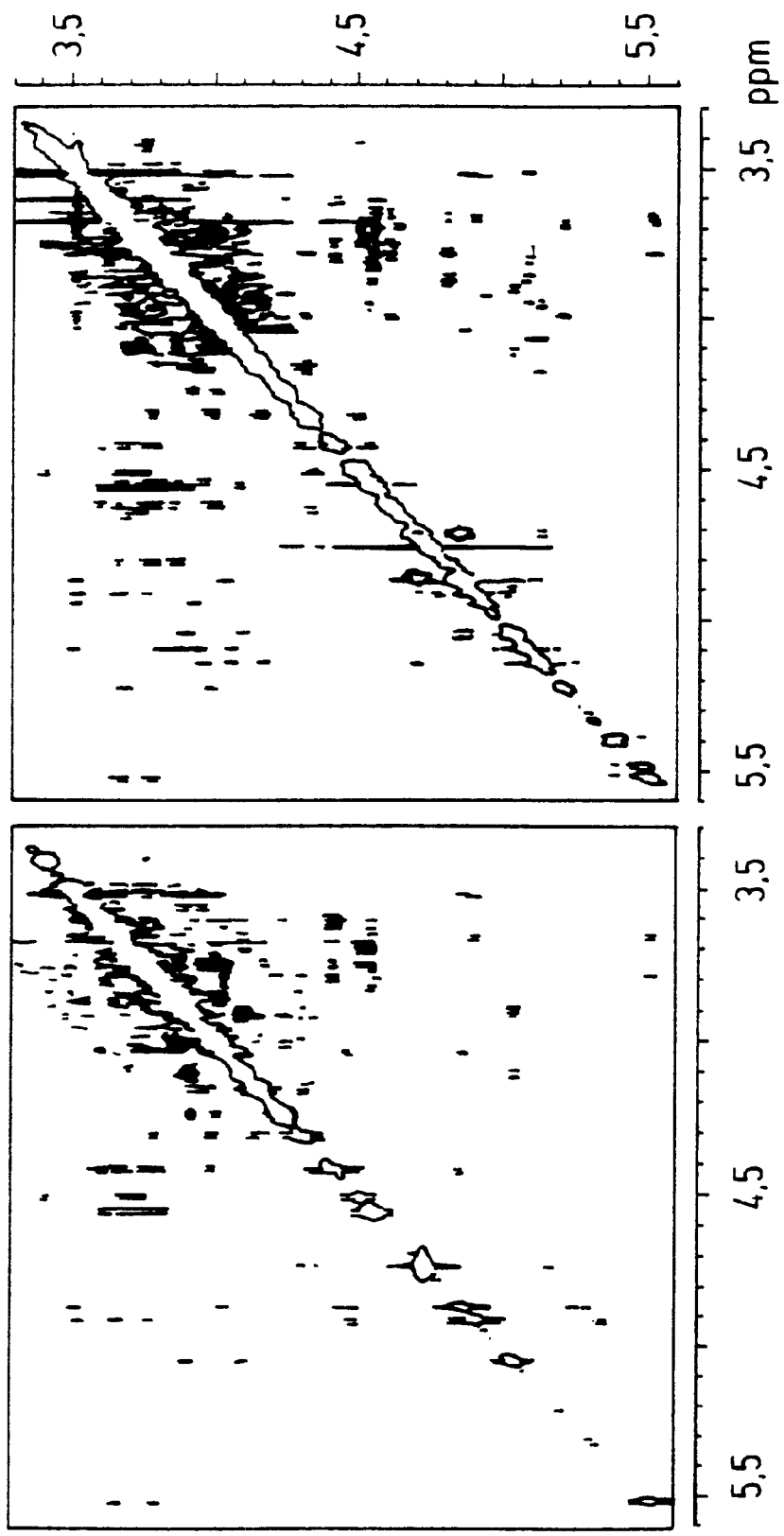
FIG. 2a shows a 2D-NOESY-spectrum of a mixture of six different saccharides that contain the disaccharide from FIG. 1 (compound library A)
FIG. 2b shows a 2D-NOESY-spectrum of a mixture of 15 different saccharides that contain the disaccharide from FIG. 1 (compound library B)

FIG. 2 shows the 2D-NOESY-spectra that were obtained for the libraries A (FIG. 2a) and B (FIG. 2b) in the absence of the lectin receptor. These proton NMR-spectra display strong overlap of all signals. The NOE-pattern of the sought disaccharide cannot be identified.

FIG. 3 shows the 2D-trNOESY-spectra of the compound libraries A (FIG. 3a) and B (FIG. 3b) in the presence of a lectin. The NOE-pattern of the sought disaccharide is now clearly visible (compare also FIG. 4), because the cross-peaks that are characteristic for the disaccharide are situated distantly from the background signals. The signal pattern obtained can be used to identify the ligand as this is shown for the case of disaccharide 1 that is shown in FIG. 1.

Figure 4:
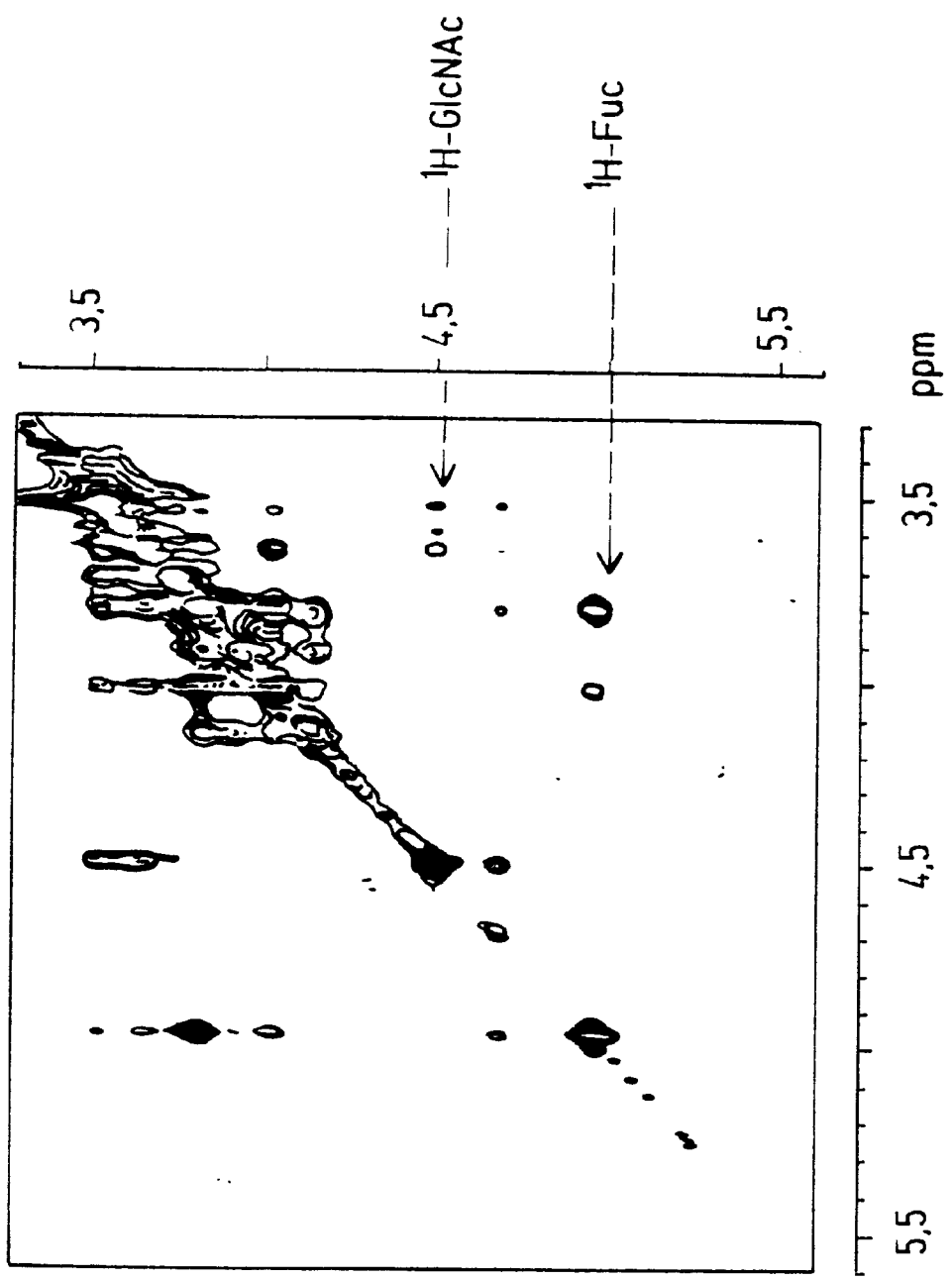
FIG. 4 shows a 2D-trNOESY-spectrum of the disaccharide of FIG. 1 in presence of the receptor AAA.

In FIG. 4 2D-trNOESY spectrum of the receptor-ligand complex from disaccharide 1 (ligand) and lectin AAA (receptor) is shown. In FIG. 4 two typical cross peaks are designated that clearly show the trNOE. The one that is designated $^1$H-Fuc designates the crosspeak that is associated with a proton at $C_1$ of the fucose residue.

The cross peak that is designated with $^1$H-GlcNAc can be assigned to the proton that is attached to the $C_1$-atom of the glucosamine residue.

Comparison of FIG. 4 with FIG. 3 allows immediate identification of the ligand that is disaccharide 1 in both compound libraries A and B. The compounds that do not bind to the receptor have small positive NOE signals that are not visible in the present spectra.

In this case, the identification of the ligand (disaccharide 1) in the compound libraries A and B is possible via comparison of FIG. 3 and 4 and is especially easy. It is clearly visible that the disaccharide that is shown in FIG. 1 binds to the lectin AAA and that neither library A nor library B contain other compounds that bind to the lectin, because otherwise further trNOE-peaks would be observed.

It follows that the method of the invention allows to unambiguously identify a ligand in a compound mixture using an added receptor.

In cases where the ligand and its proton NMR spectra are not known, other NMR experiments must follow which allow identification of the compound and the analysis of the compound's structure. The magnetization that is present at the end of the trNOE-pulse sequence and that is only present for the bound compounds can be used to subsequently perform classical 2D-NMR-experiments (TOCSY, COSY, HMQC). These experiments can either be performed as 3D-NMR-experiments or with advantage as 1D- or 2D-variants of 3D-experiments.

What is claimed is:

1. A method for detecting at least one ligand present in a compound library using at least one receptor that binds to said ligand by creating a ligand-receptor complex, comprising the steps of:
    a) adding to said compound library a particular receptor having a substantially higher molecular weight than a particular ligand to be identified, thereby creating a ligand-receptor complex within the mixture, and
    b) performing, on the mixture resulting from step a), a spectroscopic measurement technique to detect dipolar resonance phenomena that occur upon a binding of said ligand to said receptor, said phenomenon being the transfer nuclear Overhauser effect (trNOE), said technique being performed without isolating the ligand-receptor complex from said mixture, thereby detecting said ligand.

2. The method of claim 1, wherein said spectroscopic measurement technique is a nuclear magnetic resonance (NMR) spectroscopy.

3. A method for detecting at least one ligand present in a compound library using at least one receptor that binds to said ligand by creating a ligand-receptor complex, comprising the step of:
    a) adding to said compound library a particular receptor having a substantially higher molecular weight than a particular ligand to be identified, thereby creating a ligand-receptor complex within the mixture, and
    b) performing, on the mixture resulting from step a), a spectroscopic measurement technique to detect dipolar resonance phenomena that occur upon a binding of said ligand to said receptor, said phenomenon being the transfer electron nuclear Overhauser effect, said technique being performed without isolating the ligand-receptor complex from said mixture, thereby detecting said substance.

4. The method of claim 1, wherein the trNOE is measured by a two-dimensional NOE spectroscopic experiment.

5. The method of claim 4, wherein the two-dimensional NOE spectroscopic experiment is a 2D-NOESY experiment.

6. The method of claim 4, wherein the two-dimensional NOE spectroscopic experiment is a 2D-ROESY experiment.

7. The method of claim 1, wherein the trNOE is part of a multi-dimensional homo- or hetero nuclear experiment.

8. The method of claim 7, wherein one or more evolution times are kept constant during said experiment to reduce the dimensionality of the experiment.

9. The method of claim 1, wherein the trNOE is measured in a one-dimensional experiment.

10. The method of claim 2, wherein one or more high frequency pulses are applied selectively or band selectively.

11. The method of claim 5, wherein the 2D-NOESY spectrum of the compound library in the presence of said receptor is measured with a mixing time that is shorter than 500 milliseconds.

12. The method of claim 1, wherein said ligand is a low molecular weight substance, whose molecular weight is less than about 2000 Da.

13. The method of claim 1, wherein said receptor is a high molecular weight substance, whose molecular weight is greater than about 15000 Da.

14. The method of claim 1, wherein said receptor is composed of several high molecular weight substances, whose molecular weight is each greater than about 15000 Da.

15. The method of claim 1, wherein said receptor is a substance that is embedded into a higher molecular weight aggregate, whose total molecular weight is greater than about 15000 Da.

16. The method of claim 1, wherein said receptor is embedded in cell fragments or whole cells.

17. The method of claim 1, wherein said compound library is composed of natural substances that are selected from the group consisting of peptides, proteins, nucleic acids, carbohydrates, lipids, and substances having a molecular weight of less than approximately 2000 Da selected from the group consisting of whole cells, organells, cell extract, whole bacteria, bacterial extracts, viruses, viral extracts, body fluids and mixtures of these substances.

18. The method of claim 1, wherein said compound library is composed of synthetic materials.

19. The method of claim 1, wherein, if said detecting is performed on unknown ligands, additional one- or two-dimensional nuclear magnetic resonance (NMR) experiments are performed for identifying the ligand or for identifying the ligand-receptor complex, wherein said experiments are performed either before or after a dipolar resonance transfer has occurred.

* * * * *